United States Patent [19]

Shofner et al.

[11] Patent Number: 6,029,316
[45] Date of Patent: Feb. 29, 2000

[54] ENVIRONMENTAL CONDITIONING METHODS AND APPARATUS FOR IMPROVED MATERIALS TESTING: RAPIDCON AND RAPIDAIR

[75] Inventors: Frederick M. Shofner; Betty Jo N. Shofner, both of Knoxville, Tenn.; Michael D. Watson, Raleigh, N.C.

[73] Assignee: Premier Polytronics Limited, India

[21] Appl. No.: 09/002,513

[22] Filed: Jan. 2, 1998

Related U.S. Application Data

[60] Provisional application No. 60/034,022, Jan. 8, 1997.

[51] Int. Cl.⁷ .................................................. D01B 3/04
[52] U.S. Cl. .............................................. 19/66; 19/65 A
[58] Field of Search ............................... 19/66 R, 66 CC, 19/65 A, 200; 73/160, 865.6

[56] References Cited

U.S. PATENT DOCUMENTS

| | | |
|---|---|---|
| 4,512,060 | 4/1985 | Shofner . |
| 4,527,306 | 7/1985 | Thannheiser ........................ 19/66 CC |
| 4,631,781 | 12/1986 | Shofner . |
| 4,686,744 | 8/1987 | Shofner . |
| 5,121,522 | 6/1992 | Leifeld et al. . |
| 5,138,879 | 8/1992 | Shofner et al. ........................... 73/160 |
| 5,157,910 | 10/1992 | Artzt et al. ............................... 19/66 R |
| 5,321,496 | 6/1994 | Shofner et al. ........................... 19/200 |
| 5,361,450 | 11/1994 | Shofner et al. . |
| 5,537,868 | 7/1996 | Shofner et al. . |
| 5,560,194 | 10/1996 | Shofner et al. . |
| 5,676,177 | 10/1997 | Shofner et al. . |

OTHER PUBLICATIONS

Shofner et al International Application No. PCT/US 95/13796 Published Under the Patent Cooperation Treaty (PCT) as International Publication NO. WO 96/14262 on May 17, 1996.

J.L. Knowlton and Roger K. Alldredge, "Experience with Rapid Conditioning of HVI Samples," Beltwide Cotton Conference, San Diego, California, Jan. 1994.

Darryl W. Earnest, "Advancements in USDA Cotton Classing Facilities," Engineered Fiber Conference, Raleigh, North Carolina, May 1996.

Michael D. Watson, Robert S. Baird and Frederick M. Shofner, "Australian and American Experience with RapidCon©," presented at the Beltwide Cotton Conferences, New Orleans, Louisiana, Jan. 9, 1997.

*Primary Examiner*—William Stryjewski
*Assistant Examiner*—Gary L. Welch
*Attorney, Agent, or Firm*—Carter & Schnedler, P.A.

[57] ABSTRACT

Methods and apparatus for effecting sample-specific cycles for the environmental conditioning of material samples, such as cotton samples, prior to testing; and for the environmental conditioning of testing laboratory space, a subspace or "oasis zone" within the testing laboratory space and/or a test zone within a testing machine. A sensor measures at least one material property of the sample, such as moisture content of a cotton sample. Based on the material property, a sample-specific conditioning cycle is determined and effected by driving through the sample a gas flow conditioned as to at least one parameter which affects properties of the sample, such as a temperature, relative humidity, and volume per unit time, and all of which are relevant in the case of a cotton sample. The determined conditioning cycle is a cycle which causes the sample to be conditioned to an optimum state for testing, and includes a sequence of time intervals in which sequence at least one of the selected parameters varies from one time interval to the next. A combination sample conditioning and air conditioning machine includes an environmental chamber for conditioning a sample for testing, and conditioned air discharge ports for directing conditioned air to the testing laboratory space, the oasis zone, and the test zone, as well as a return air port. Gas flow conditioning apparatus directs conditioned gas flows through the environmental conditioning chamber and out through the conditioned air discharge port.

34 Claims, 7 Drawing Sheets

ENVIRONMENTAL CONDITIONING METHODS AND APPARATUS FOR IMPROVED MATERIALS TESTING: RAPIDCON AND RAPIDAIR

CROSS-REFERENCE TO PROVISIONAL PATENT APPLICATION

The benefit of U.S. Provisional Application Ser. No. 60/034,022, filed Jan. 8, 1997, is claimed.

BACKGROUND OF THE INVENTION

The apparatus and methods disclosed herein are applicable, in general, to the field of material property testing, more specifically to the area of environmental conditioning of material samples or of laboratory space and instrument test zones wherein testing takes place, and most specifically, for the preferred embodiment, rapid environmental conditioning of cotton fiber, yarn, or fabric samples and the laboratories or test zones of instruments in which they are tested.

It is well known that the conditions or state of samples undergoing material property testing strongly affect test results. Rigorous and reproducible sample preparation are critical to obtaining precise and accurate test results. Major factors in sample preparation are the precision and accuracies of environmental conditions in which these steps take place. It is also well known that environmental conditions in the testing zones of materials property testing laboratories or instruments can strongly affect test results. This fact is generally important for fiber testing, and particularly critical for cotton, and other natural fibers, and for rayon, and other man-made fibers. Methods and apparatus for controlling testing zone environmental conditions are described in several U.S. patents of the first-named inventor herein and others, and in other published literature, briefly discussed below.

The prior disclosures are based in part on a recognition that it is environmental conditions within testing zones that must be accurately, precisely, cost-effectively, or optimally controlled, rather than environmental conditions in the testing laboratory. Embodiments are disclosed which enable realization of improved environmental conditions within the testing zones. Thus, Shofner U.S. Pat. No. 4,631,781, Leifeld et al U.S. Pat. No. 5,121,522, and Shofner et al U.S. Pat. No. 5,361,450, the entire disclosures of which are hereby expressly incorporated by reference, disclose improvements for the textile fiber materials processing machine step known as carding. Shofner U.S. Pat. No. 4,631,781 and Shofner et al U.S. Pat. No. 5,537,868, the entire disclosures of which are hereby expressly incorporated by reference, disclose embodiments relating to fiber testing instruments. Shofner et al U.S. Pat. No. 5,910,598, International Application No. PCT/US 95/13796 published May 17, 1996 as International Publication No. WO 96/14262, and Shofner et al U.S. Pat. No. 5,676,177, the entire disclosures of which are hereby expressly incorporated by reference, disclose improvements for textile weaving machines. Shofner et al U.S. Pat. No. 5,560,194, the entire disclosure of which is hereby expressly incorporated by reference, discloses optimal process control methods for spinning machines.

The subject invention is primarily disclosed in the context of improvements in environmental control methods and apparatus for fiber testing, which are representative of materials testing in general. Accordingly provided next is a brief background information relating to "rapid conditioning," a sample preparation step for instrument classification of cotton for HVI testing. Facilitating and improving this sample preparation step is an objective of the subject invention. Commercial embodiments of such rapid conditioning apparatus may be called "RapidCon." Another objective of the invention is to advantageously combine sample conditioning with laboratory space and instrument test zone environmental conditioning. Commercial embodiments of such multiple purpose apparatus which provides air conditioning of external laboratory space and rapid conditioning of internal test samples may be called "RapidAir."

Various United States Department of Agriculture papers describe a major improvement in fiber testing methods, known as "rapid conditioning," wherein sample condition times are reduced from 72 or 48 hours to 15 minutes or less. Examples are J. L. Knowlton and Roger K. Alldredge, "Experience with Rapid Conditioning of HVI Samples," Beltwide Cotton Conference, San Diego, Calif., January 1994; and Darryl W. Earnest, "Advancements in USDA Cotton Classing Facilities," Engineered Fiber Conference, Raleigh, N.C., May 1996.

Before this "rapid conditioning," for more than seventy-five years, certain fiber, yarn, or fabric tests have been conducted under so-called "Standard Laboratory Environment" or ASTM conditions of 65% relative humidity and 70° F. (21° C.) dry bulb temperature. Since what matters most, for good test results, is not conditions in the lab but conditions in the samples (and within the testing zones) at the time of testing, the various ASTM methods for fiber, yarn, or fabric samples further include the requirement that the samples to be tested be stored or "conditioned" in the standard environment for 72 hours prior to testing in the standard environment. This storage time presumably allows the samples to "reach equilibrium." It is noted that samples so conditioned are passively equilibrating, and that equilibrium usually refers to sample moisture content. Moisture content is the weight of water in the sample as a percentage of the dry weight of the sample. For cotton, equilibrium moisture content MC is about 7.3% at 65% RH, 70° F. (21° C.).

It should however be noted that moisture content is only one fiber, yarn, or fabric material property measurement whose equilibrium value is of interest. Others include tenacity and length (for fibers), and such material properties are much more important for selling, buying and using the fibers than is moisture content. We emphatically note that moisture content affects other fiber material properties, and is therefore an important control variable, but is not as important for marketing or utilization purposes.

Whereas equilibration times of 72 hours yield the best and most consistent test results, such periods are unacceptably long in today's intensely competitive and information-hungry marketplace. It is therefore critically important that the tests be executed accurately and precisely, that is, with minimal bias or random errors. But testing before equilibria in the tested properties are reached can disastrously (in profit/loss terms) reduce accuracy and precision. (We note that equilibrium times are different for different materials test parameters.)

Recognizing the severe conflict between promptly available results versus good (precise and accurate) results, the United States Department of Agriculture Agricultural Marketing Service, Cotton Division, began investigations in the early 1990's into actively and rapidly conditioning cotton samples. These investigations were remarkably successful and proved that well-conditioned laboratory air could be actively drawn through HVI samples (as opposed to passive or diffusional mass and heat transfer), which active conditioning or "rapid conditioning" enabled samples to reach moisture content or strength equilibrium in less than about 15 minutes. The Knowlton et al and Earnest literature references cited above provide a description. "Rapid conditioning" is now employed in most of the fourteen USDA/AMS cotton classing offices.

In our efforts to extend USDA results to small instrument classing operations having one to four HVIs (versus twenty to forty), and not having well-conditioned laboratories, we discovered that simply drawing 65%, 70° F. (21° C.) air through the samples for 15 minutes yielded unacceptable test results for dry and wet samples, and that unacceptably long conditioning times were required to achieve good results. We also found that sample type and size affected test results and conditioning times. Still further, we found that samples having a moisture content near 7.3% did not require much, if any, rapid conditioning. And, on a practical economic basis, we found that many small laboratories could not afford expensive laboratory or test zone environmental controls.

SUMMARY OF THE INVENTION

Accordingly, it is an object of the invention to provide for complex, sample-specific conditioning cycles which optimize test results and minimize active conditioning times.

Another object of the invention is to combine, in one cost-effective machine, internal sample conditioning and external air conditioning capability for laboratory space and instrument test zones.

In overview, a general aspect of the invention is a method for processing materials in a machine, where the materials are conditioned for subsequent testing. The materials are presented to a measurement station, where one or more material properties are measured. From a machinery model, an environmental conditioning cycle is determined in advance which causes the materials to be processed into an optimum state for either concurrent or subsequent testing, the environmental conditioning cycle relating to temporal and spatial characteristics of one or more environmental parameters which control the material properties.

The materials are transported and presented to an environmental conditioning zone. Within the environmental conditioning zone a gas flow is deliberately applied to the materials, the gas flow being conditioned by one or more parameters which control the material properties, and with the application cycle for each of the one or more controlling parameters having been previously determined. The materials are tested in one or more subsequent machine steps.

In accordance with a more particular aspect, the invention provides a method for conditioning a sample of cotton fiber for testing. The method includes the steps of measuring sample moisture content and, based on the measured moisture content, determining a conditioning cycle and effecting the conditioning cycle by driving a conditioned gas flow through the sample, the conditioned gas flow being conditioned as to at least one parameter selected from the group consisting of temperature, relative humidity, volume per unit time, and time duration. Preferably, the determined conditioning cycle is a cycle which causes the sample to be conditioned to an optimum state for testing, and includes a sequence of time intervals, in which sequence at least one of the selected parameters varies from one time interval to the next. In accordance with the method, sample moisture content may be measured prior to determining and effecting the conditioning cycle, or sample moisture content may be measured concurrently with determining and effecting the conditioning cycle.

In one embodiment, a plurality of samples of cotton fiber are similarly measured and similarly conditioned, for example twenty-four samples in a perforated-bottom sample tray are similarly measured and similarly conditioned.

The invention also provides a corresponding machine for conditioning a sample of cotton fiber for testing. The machine includes a sensor for measuring sample moisture content, and a controller for determining a conditioning cycle based on measured moisture content. Gas flow conditioning apparatus effects the conditioning cycle by driving a conditioned gas flow through the sample, the conditioned gas flow being conditioned as to at least one parameter selected from the group consisting of temperature, relative humidity, volume per unit time, and time duration. Preferably, the controller determines a conditioning cycle which causes the sample to be conditioned to an optimum state for testing. The conditioning cycle may include a sequence of time intervals during which sequence at least one of the selected parameters varies from one time interval to the next.

In accordance with another aspect, the invention provides a method for conditioning a sample of fiber for testing. The method includes the steps of measuring at least one property of the fiber sample selected from the group of properties consisting of weight, moisture content, nep content, trash content, fiber tenacity, fiber strength, fiber length, calorimetric properties, air flow permeability properties, near-infrared reflectance, and imaged characteristics. Based on the measured fiber property, a conditioning cycle is determined, and effected by driving a conditioned gas flow through the sample. The gas flow is conditioned as to at least one parameter selected from the group consisting of humidity, temperature, static pressure, pressure fluctuations, velocity, velocity fluctuations, gas composition, radioactive particle concentration, and time duration.

Preferably, the determined conditioning cycle is a cycle which causes the fiber sample to be conditioned to an optimum state for testing. The determined conditioning cycle includes the specification of temporal and spatial characteristics of at least one gas flow parameter which affects properties of the fiber sample. The conditioning cycle may include a sequence of time intervals during which sequence at least one of the selected parameters varies from one time interval to the next.

The sample property may be measured prior to determining and effecting the conditioning cycle, or the sample property may be measured concurrently with determining and effecting the conditioning cycle.

The invention additionally provides a corresponding machine for conditioning a sample of fiber for testing. The machine includes a sensor for measuring at least one property of the sample selected from the group of properties consisting of weight, moisture content, nep content, trash content, fiber tenacity, fiber strength, fiber length, calorimetric properties, air flow permeability properties, near-infrared reflectance and imaged characteristics. There is a controller for determining a conditioning cycle based on the at least one property of the sample, and gas flow conditioning apparatus for effecting the conditioning cycle by driving a conditioned gas flow through the sample. The conditioned gas flow is conditioned as to at least one parameter selected from the group consisting of humidity, temperature, static pressure, pressure fluctuations, velocity, velocity fluctuations, gas composition, radioactive particle concentration and time duration.

Preferably, the controller determines a conditioning cycle which causes the fiber sample to be conditioned to an optimum state for testing. The conditioning cycle determined by the controller incudes the specification of temporal and spatial characteristics of at least one gas flow parameter which affects properties of the fiber sample. The conditioning cycle may include a sequence of time intervals during which sequence at least one of the selected parameters varies from one time interval to the next.

In accordance with yet another aspect, the invention provides a method for conditioning a sample of material for testing. The method includes the steps of measuring at least one material property of the sample and, based on the material property, determining a conditioning cycle and effecting the conditioning cycle by driving through the sample a gas flow conditioned as to at least one parameter. Preferably, the determined conditioning cycle is a cycle which causes the sample to be conditioned to an optimum state for testing. The determined conditioning cycle includes the specification of temporal and spatial characteristics of at least one gas flow parameter which affects properties of the samples. The conditioning cycle may include a sequence of time intervals, during which sequence at least one of the parameters varies from one time interval to the next. The material property may be measured prior to determining and effecting the conditioning cycle, or the material property may be measured concurrently with determining and effecting the conditioning cycle.

The invention provides a corresponding machine for conditioning a sample of material for testing. The machine includes a sensor for measuring at least one material property of the sample, and a controller for determining a conditioning cycle based on the material property. Gas flow conditioning apparatus is provided for effecting the conditioning cycle by driving through the sample a gas flow condition as to at least one parameter. The controller determines a conditioning cycle sample to be conditioned to an optimum state for testing. The conditioning cycle includes the specification of temporal and spatial characteristics of at least one gas flow parameter which affects properties of the sample. The conditioning cycle includes a sequence of time intervals during which sequence at least one parameter varies from one time interval to the next. The material property may be measured prior to determining and effecting the conditioning cycle, or the material property may be measured concurrently with determining and effecting the conditioning cycle.

In yet another aspect, the invention provides a combination sample conditioning and air conditioning machine including an environmental conditioning chamber within the machine for conditioning a material sample. The machine has at least one conditioned air discharge port for directing conditioned air to at least one of the zones selected from the group consisting of a testing laboratory space, an oasis zone within the testing laboratory space, and a test zone within a testing machine. At least one return air port collects air from at least one of the zones. The combination machine additionally includes gas flow conditioning apparatus for directing conditioned gas flows through the environmental conditioning chamber and out through the conditioned air discharge port. Control elements within the machine adjust the gas flows through the ports.

In accordance with another aspect, the combination machine additionally includes a sensor for measuring at least one property of the material sample, and a controller for determining a conditioning cycle based on the measured property. The gas flow conditioning apparatus effects the conditioning cycle by driving through the sample a gas flow conditioned as to at least one parameter. Preferably, the controller determines a conditioning cycle which causes the sample to be conditioned to an optimum state for testing.

Aspects of the subject invention were disclosed in a paper by Michael D. Watson, Robert S. Baird and Frederick M. Shofner, "Australian and American Experience with RapidCon™," presented at the Beltwide Cotton Conferences, New Orleans, La., Jan. 9, 1997.

BRIEF DESCRIPTION OF THE DRAWINGS

While the novel features are set forth with particularity in the appended claims, the invention, both as to organization and content, will be better understood and appreciated from the following detailed description, in conjunction with the drawings, in which:

DETAILED DESCRIPTION

Figure 2:
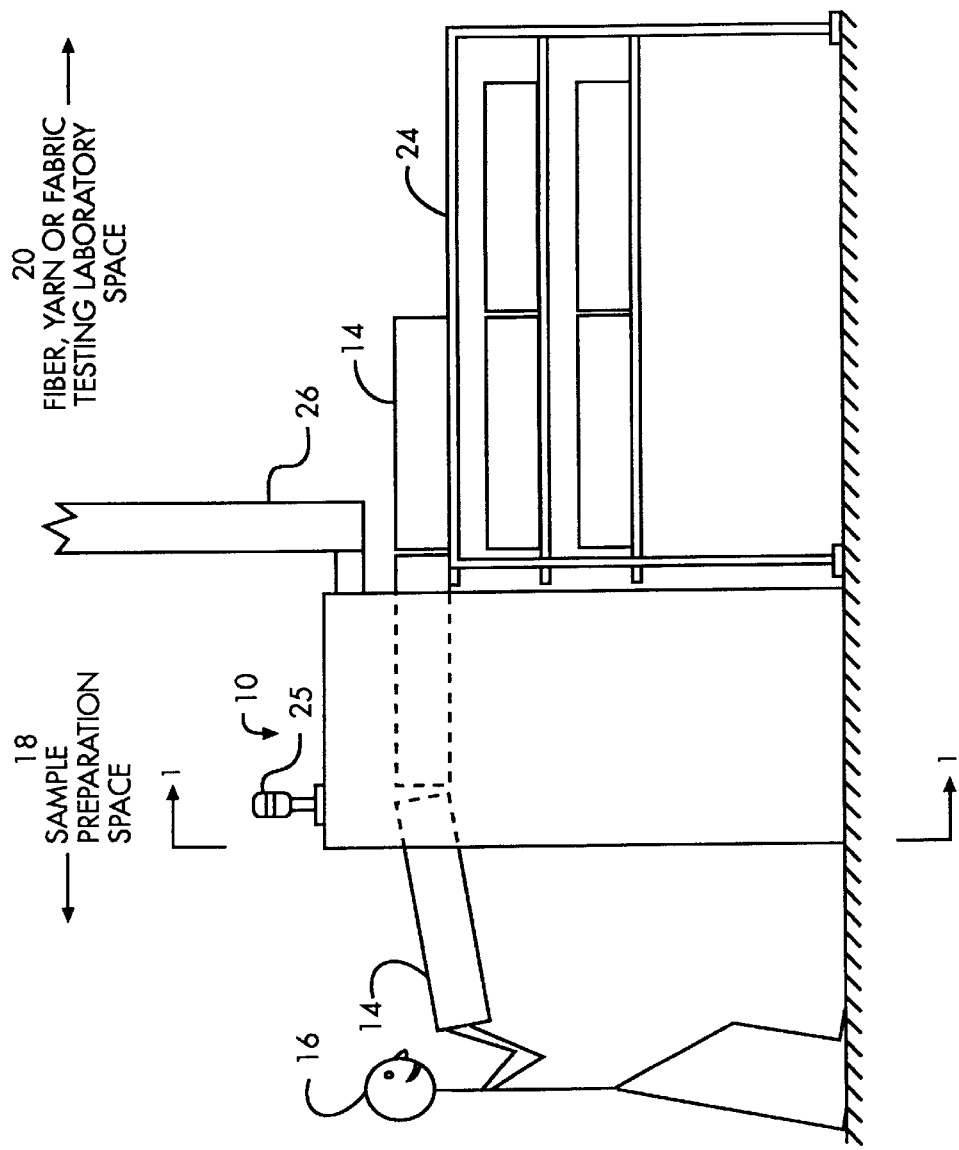
FIG. 2 is a right side view of the sample conditioning machine of FIG. 1.
Figure 1:
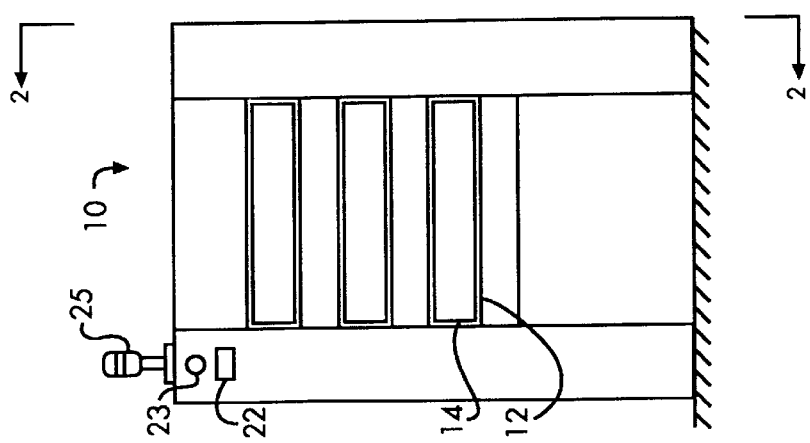
FIG. 1 is a front elevational view of a sample conditioning machine.

FIGS. 1 and 2 are front and right side views of a sample conditioning machine 10 having three identical, vertically-organized stages 12 upon which sit perforated bottom sample trays 14. For High Volume Instrument (HVI) cotton classing samples, the sample trays 14 are preferably 32×32×6 inches (81×81×15 cm), constructed of light-weight yet strong cardboard or plastic, and have about 25% or more of their bottom areas perforated with holes (not shown). The holes restrain or hold the samples, while permitting relatively unrestricted air flows. A preferred tray bottom consists of $1/16$ inch (1.6 mm) thick perforated aluminum having $1/8$ inch (3.2 mm) holes with $3/16$ inch (4.8 mm) centerline spacing (staggered). Typically twenty four HVI samples, each weighing about 0.25 to 0.75 pounds (0.113 to 0.340 kg), are placed in a 6×4, side-by-side and closely spaced configuration within each tray 14. Yarn, fabric or other material samples may similarly be placed in sample tray 14.

A stick-man operator 16 in FIG. 2 suggests general size and proportions of a machine 10 having a height of 72 inches (183 cm) and a depth of 34 inches (86 cm). Width seen in FIG. 1 is about 54 inches (137 cm). FIG. 2 also suggests how the operator 16 loads sample trays 14 into sample conditioning machine 10 from sample preparation space 18. Upon loading trays 14, operator 16 selects the appropriate conditioning cycle with switch 23 and then presses start switch 22, whereupon machine 10 initiates and automatically executes a sample conditioning cycle. The manner in which sample specific conditioning cycles are chosen, either manually or automatically, is described more fully hereinbelow. The apparatus and methods enabling such cycles are one aspect of the invention.

Upon completion of the sample conditioning cycle, annunciator light bar 25 flashes. The operator 16 then pushes sample trays 14 onto a rack 24, which sits in testing laboratory space 20. The next batch of sample trays 14 may then be loaded, whereupon the operator 16 again selects the appropriate sample conditioning cycle with switch 23 and presses start switch 22 to initiate that cycle.

Figure 4:
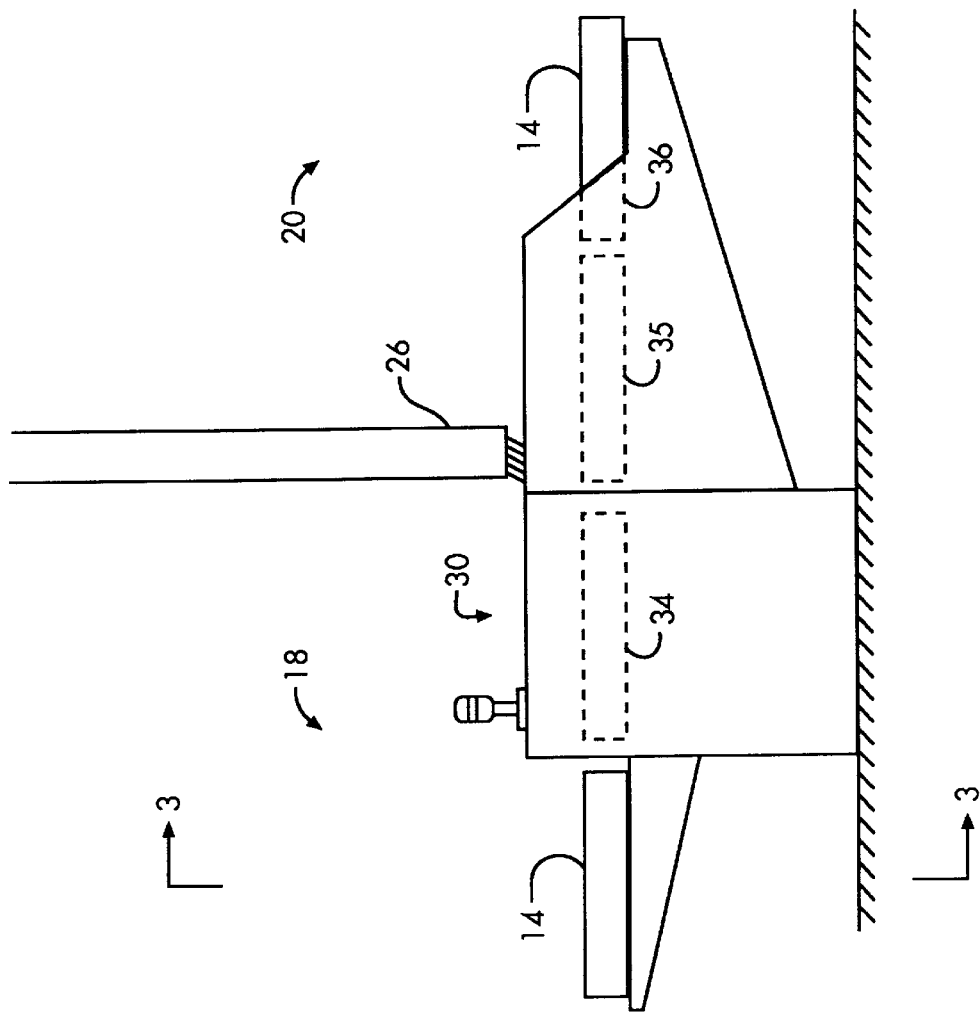
FIG. 4 is a right side view of the sample conditioning machine of FIG. 3.
Figure 3:
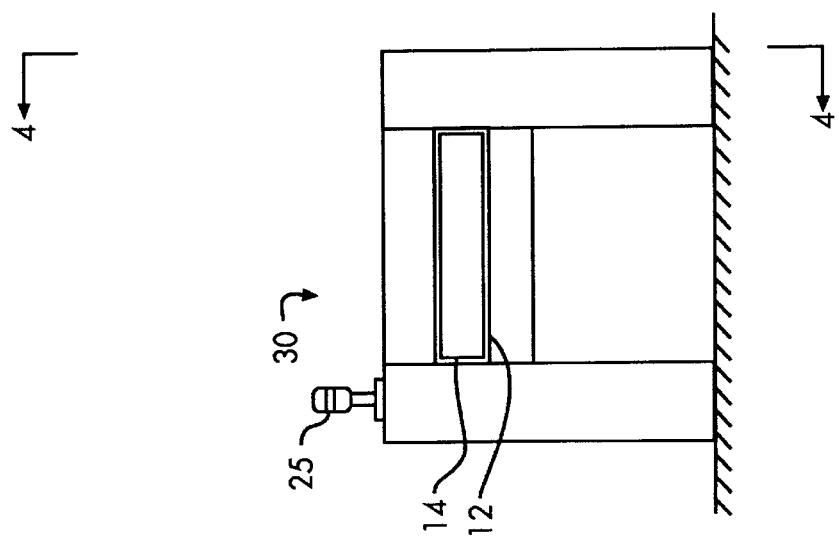
FIG. 3 is a front elevational view of a horizontally-organized sample conditioning machine.

FIGS. 3 and 4 show a horizontally-organized sample conditioning machine 30, also having three processing stages 34, 35, 36 for sample trays 14. Gas flow conditions may be different or the same for the stages 34, 35, 36. Conditioning cycle selection procedures and sample conditioning processing rates are identical for machine 10 of FIGS. 1 and 2 and machine 30 of FIGS. 3 and 4.

Machine configuration 10 of FIGS. 1 and 2, and machine configuration 30 of FIGS. 3 and 4, serve to condition material samples according to sample-specific conditioning cycles, details of which are described hereinbelow with reference to FIG. 7.

Figure 5:
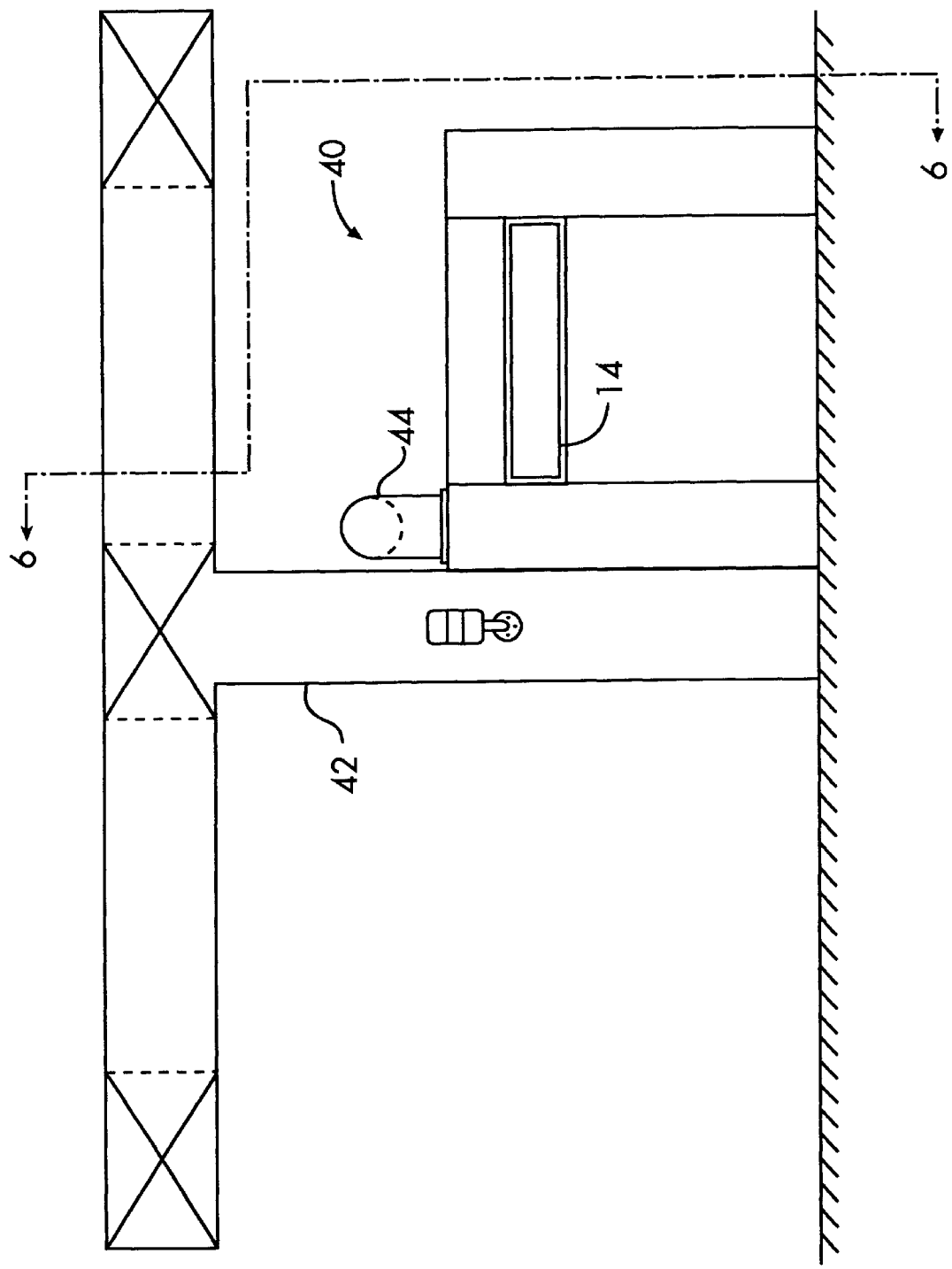
FIGS. 5 and 6 depict an integrated sample conditioning and air conditioning machine.
Figure 6:
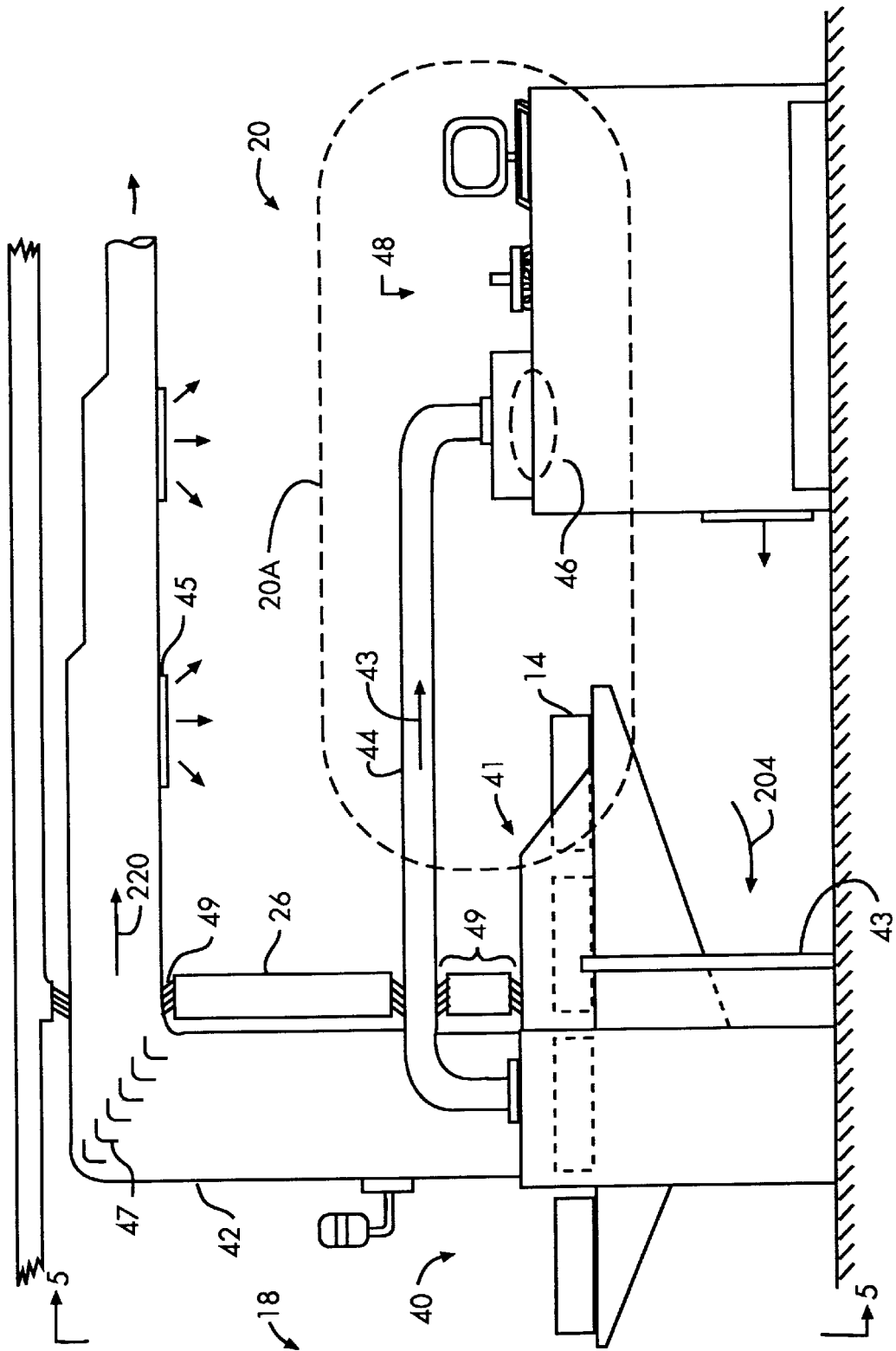

With reference to FIGS. 5 and 6, an additional function is served by an integrated sample conditioning and air conditioning machine 40. Sample preparation space 18 and testing laboratory space 20 are typically divided by wall 26. It is usually not essential that sample preparation space 18 be well-conditioned. Testing laboratory space 20 must be well-conditioned, with standard environmental conditions, as described in the prior art background. Rigidly controlled testing laboratory 20 conditions, coupled with rigidly-controlled internal test zone conditions 46, are advantageous in terms of costs and performance, and this is enabled by the integrated machine 40 of the invention. Test zone environmental control using movable conditioning apparatus is described in the above-incorporated Shofner et al U.S. Pat. No. 5,537,868. The apparatus of the invention can provide the conditioned gas flows for such test zone 46 environmental controls and for testing laboratory space 20.

In FIG. 6, conditioned sample tray 14 delivery 41 is into laboratory space 20, which space 20 is conditioned entirely or partly by air distributed from supply ductwork 42. Conditioned gas flows 220 in duct 42 are provided by machine 40, as are conditioned flows 43 in duct 44 for internal environmental controls in one or more test zones 46 in testing instrument 48. Testing instrument 48 may test fibers, yarn, fabric, or other materials. For fiber testing, to which this preferred embodiment is directed, testing instrument 48 may be High Volume Instrument (HVI), an Advanced Fiber Information System (AFIS), or a RapidTester as disclosed in Shofner et al U.S. Pat. Nos. 5,890,264 and 5,929,460. HVI instruments are manufactured by Zellweger Uster Inc., Knoxville, Tenn., U.S.A.; and by Premier Polytronics Limited, Coimbatore, India. AFIS is manufactured by Zellweger Uster Inc. RapidTester is manufactured by Premier Polytronics Limited.

A sub-space 20A of testing laboratory space 20, termed herein an "oasis zone" 20A, is of particular practical importance; the accuracy and precision of environmental conditions in this sub-space 20A may be much more rigidly and cost-effectively controlled. Outside oasis zone 20A, conditions may be relaxed. Once conditioned internally by sample conditioning machine 40, the samples remain in rigidly-controlled environments of the oasis zone 20A or test zone(s) 46 until testing is finished. "Oasis Zones" 20A are particularly cost-effectively enabled by the subject invention.

Conditioned gas flows supplied to lab space 20 (including the oasis zone 20A) and test zone 46 by, typically, well-insulated ducts 42, 44, are returned 204 to sample conditioning and air conditioning machine 40 through return air grill(s) 45A. Well known but unshown air conditioning elements such as filters, dampers, and the like are used as necessary. In some cases, return air ducts are advantageous. Supply ducts 42, 44 and various grills 45, turning vanes 47, seals 49, and other such air supply and air return components chosen to meet particular, sample-specific air conditioning requirements, are well known in the art.

There are two interrelated aspects of the invention, Sample-Specific Conditioning Cycles, and Combined Sample Conditioning and Zone Air Conditioning, which are described next below.

Sample-Specific Conditioning Cycles

Our investigations into the various equilibrium processes associated with material sample conditioning and subsequent testing have revealed conditioning times and test result qualities that are dependent on sample size, sample type, beginning sample state, ending sample state, sensitivity of measured material property to environmental conditions, and the like. Using a cotton fiber example, small samples of Acala varieties which begin conditioning at 6% moisture content require far less conditioning time than large samples of Pima varieties beginning at 3% moisture content. For cotton marketing purposes, HVI strength (i.e. tenacity) and length affect buy-sell-utilization decisions more strongly. Whereas realizing equilibrium moisture content is important, we have found that it is far more important for the sample-conditioning functions of the invention to achieve higher precision and accuracy in strength and length measurements, and with shorter conditioning times.

Figure 7:
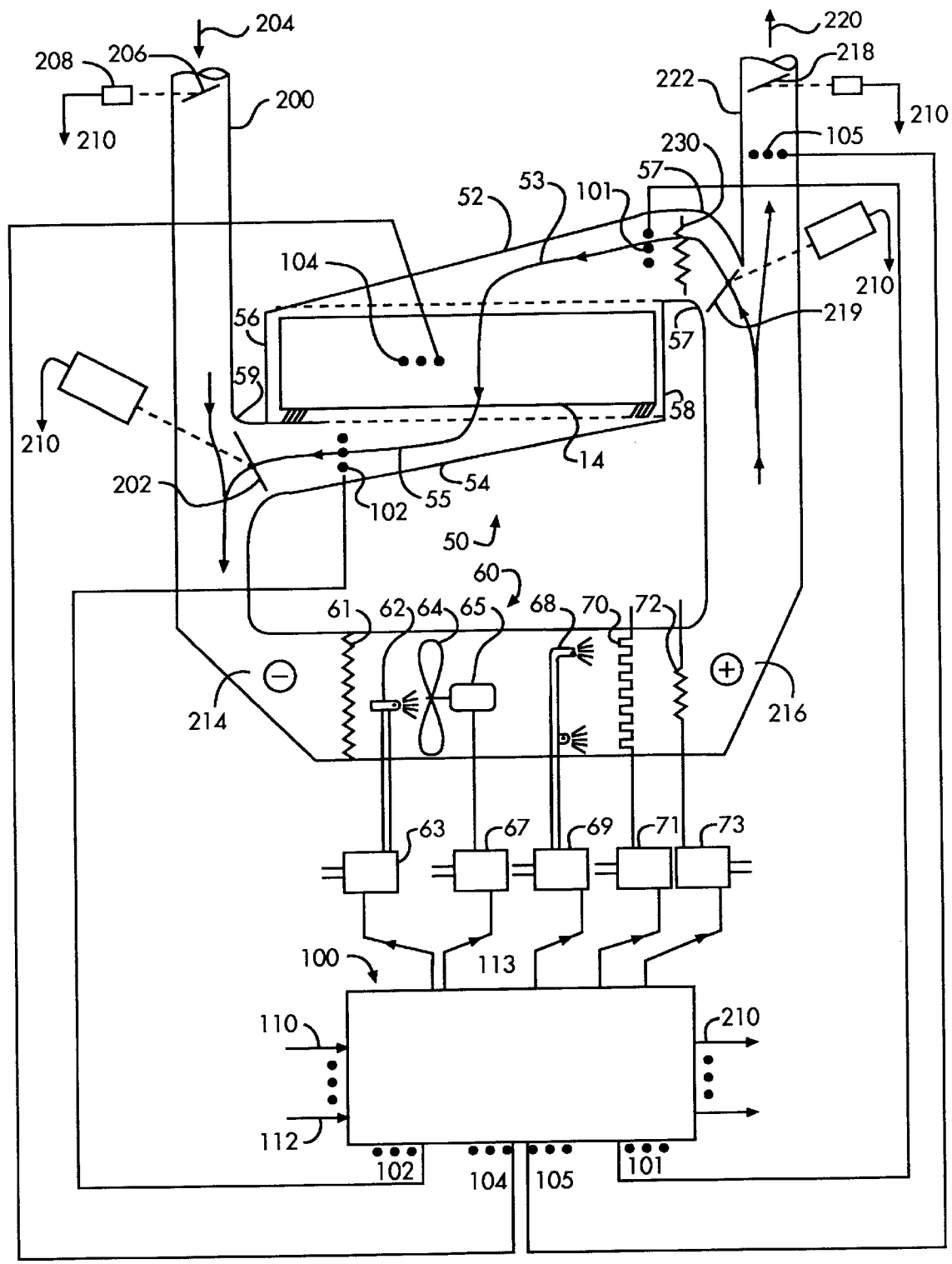
FIG. 7 depicts an embodiment sample-specific conditioning apparatus which also conditions external zones.

FIG. 7 discloses an embodiment of sample-specific conditioning apparatus, applicable to either the machine 10 of FIGS. 1 and 2, or to the machine 30 of FIGS. 3 and 4. In FIG. 7, a perforated-bottom sample tray 14, holding perhaps twenty-four cotton classing samples, each weighing about 0.25 to 0.75 pounds (0.113 to 0.340 kg), sits within sample environmental conditioning chamber 50. Sample chamber 50 is defined on the top and bottom by separator plates 52, 54, on the sides by walls 56, 58, and on the front and back by unshown doors, or in preferable practice, the fronts and backs of sample trays 14, which can be arranged for adequate sealing to minimize unwanted air flow losses or entries. Accordingly, it will be appreciated that each of the conditioning stages 12 in FIGS. 1 and 2 and in FIGS. 3 and 4 is in fact an essentially isolated environmental chamber wherein conditioning air flows enter 53 and leave 55 via entrance conduit 57 and exit conduit 59, respectively. Entering 53 and leaving 55 air flow parameters are measured by sensors 101, 102 and sample characteristics are measured prior to loading or during processing, or both, by sample sensors 104. Air flow parameter sensors 101, 102 include humidity, temperature, static pressure, velocity, and the like and particularly include sensors for the set of parameters listed in the above-incorporated Shofner et al U.S. Pat. No. 5,361,450. Sample sensors 104 include sensors for sample weight, moisture content, calorimetric properties, near-infrared reflectance (NIR), image analysis, and the like.

Sample property sensing is preferably made prior to conditioning (i.e. beginning state) but may also be performed concurrently or subsequently (ending state), to achieve more rigid control. Algorithms in microcontroller 100 can be adjusted to yield "tighter" controls according to adaptive control system methodologies. As a full extension, each of the plurality of samples may be measured and conditioned independently, when the results justify the increased costs. In usual practice, each of the plurality of samples is sufficiently like the others that average measurements are adequate to control average conditions in the entering air flow 53.

Environmental conditions in entering gas flow 53 are controlled by conventional air conditioning elements 60 preferably arranged as seen schematically in FIG. 7. For twenty-four samples, weighing about 0.5 pound (0.227 kg) each, in tray 14 (described above), volumetric air flow is about 600 ft$^3$/min (17 m$^3$/min) when the pressure difference across the samples is 3.5 inches (8.9 cm) water column. Dust filter 61, atomizer nozzle humidifier 62, fan 64, driven by motor 65, steam nozzle humidifier 68, finned cooling coil(s) 70, electrical heater element 72, and their respective control elements 63, 67, 69, 71, 73, are sized to condition flows of this magnitude and character for each stage 12. Three such stages 12 are illustrated in FIGS. 1 and 2 (vertically organized) and in FIGS. 3 and 4 (horizontally organized).

Described next is a procedural example which completes the explanation of a method enabled by apparatus as in FIG. 7. Those skilled in the art can readily create simpler or more complex cycles therefrom.

Incoming samples are placed in trays 14. The sample type, net sample weight, beginning moisture and subsequent test(s) desired are measured either manually or automatically, at one or more measuring stations, and entered into microcontroller 100, along with other sample-specific inputs via unshown keypad/display into I/O ports 110. The operator next presses the start/stop switch 22 as described above, whose binary input (contact closure) enters at I/O port 112. Microcontroller 100 then causes the sample-specific conditioning cycle program to execute control of the system 40 environmental conditioning elements (such as humidifier 68) via I/O ports such as I/O ports 113 and 210. The result of such complex, sample-specific environmental controls is improved test results for samples in trays 14 within isolated environmental conditioning chamber 50.

Figure 8:
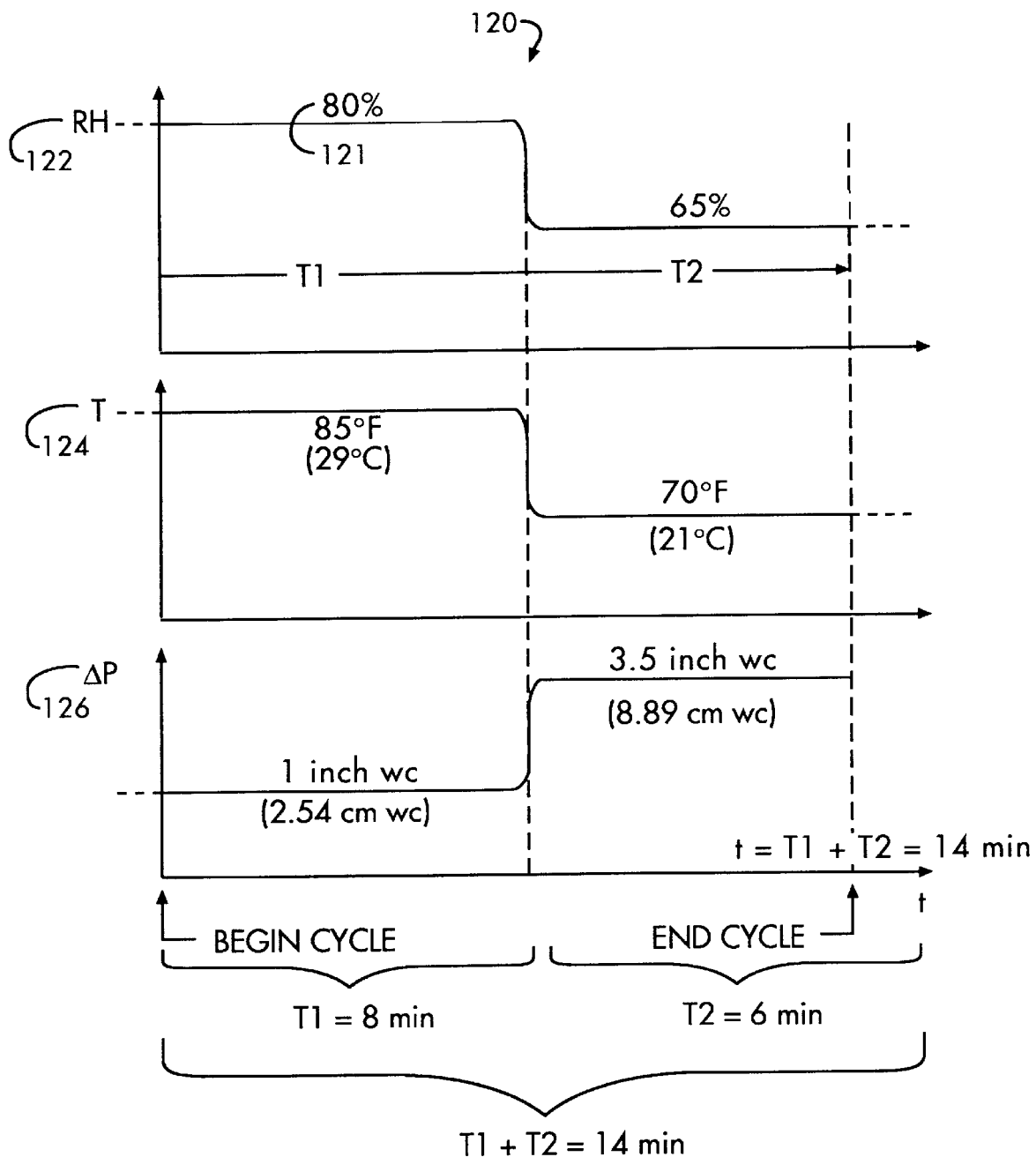
FIG. 8 is a graph plotting entering air relative humidity, dry bulb temperature, and negative static pressure as a function of time during the operation of the apparatus of FIG. 7.

FIG. 8 shows the resulting cycle temporal waveforms 120 for entering air relative humidity (RH) 122, dry bulb temperature (T) 124, and negative static pressure (suction) (ΔP) 126, including typical set-point values for intervals T1 and T2, for a dry (e.g., less than 4%) Acala variety. Thus during interval T1 of 8 minutes, entering air RH is 80% at a temperature of 85° F. (29° C.) and a suction of 1 inch (2.54 cm) water column. During interval T2 of 6 minutes, entering air RH is reduced to 65% at a reduced temperature of 70° F. (21° C.), with increased suction of 3.5 inches (8.89 cm) water column. The total cycle time T1+T2 is 14 minutes. It will be noted that the environmental conditions during interval T2 are the usual "standard" conditions.

Were these Acala samples to have moisture content of 6%, the cycle automatically selected by microcontroller 100 could omit the T1 portion. Were the samples to be dry Pima, the T1 portion of the cycle could be doubled in time duration. Were the samples to be wet Acala (9%), the relative humidity (RH) 112 set point 121 would be a relatively low 50% during the T1 portion of the cycle.

Importantly, and in summary and conclusion of this section, we have found that such sample-specific conditioning cycles produce superior HVI test results, the primary objective, and good moisture contents, and are, on average, faster. Further, yarn samples, fabric samples or material samples in general may be placed on stage 12, in tray 14, within isolated environmental chamber 50 for conditioning in accordance with the method disclosed herein.

Combined Sample Conditioning and Zone Air Conditioning

Another major objective of the invention is to provide cost-effective environmental conditioning for laboratory space 20, especially for the sub-space identified as "Oasis-Zone" 20A in FIG. 6 and for one or more test zone environments 46 in one or more testing instruments 48, in economic combination with sample conditioning, all by one machine 40 serving thereby, multiple purposes.

Sample conditioning functions are seen in FIGS. 5, 6 and 7 to be internal to machine 40 within isolated environmental chamber 50. Whereas environmental conditioning functions are enabled internally to machine 40 by conditioning apparatus 60 and control system apparatus 100, supply air flows are directed externally to laboratory space 20, 20A or instrument test zones 46 by ducts 222 (or, for clarity, ducts 42, 44 in FIG. 6). Thus, there is an economical combination for multiple purposes resulting from the isolated environmental chamber 50, and methods are implemented for enabling sample-specific conditioning cycles internally within chamber 50, with simultaneous control of external lab space 20 or sub-space 20A or test zone(s) 46.

Our discovery, and developments therefrom, began with recognition that the environmental parameters or conditions associated with sample conditioning could, by proper design and controls, be made compatible with environmental parameters or conditions associated with laboratory space or test zone conditioning. Two practical embodiments are disclosed herein, described with reference to FIGS. 7 and 9, respectively.

In the embodiment of FIG. 7, the negative pressure (suction) in exit conduit 59 is for example in the range of 0.5 to 5 inches (1.27 to 12.7 cm) water column, and is typically around 1 to 2 inches (2.54 to 5.08 cm) water column. Such suctions are satisfactory for drawing return air 204 from laboratory space 20 into inlet grill 43 (FIG. 6), through recited above but unshown filters or dampers, and into return air conduit 200. Damper 206, actuated by driver 208 under the control of microcontroller 100 through one of control signal lines 210, and damper 202 operate in concert to realize desired suctions in return conduit 200 and exit conduit 59. Fan 64, whose motor 65 is powered by a variable frequency inverter, is adjusted in speed to realize desired suction in negative plenum 214 so that dampers 202 and 206 can realize desired suctions in conduits 59 and 200.

Similarly, we designed for positive plenum 216 pressures in the range of 0.2 to 2 inches (0.508 to 5.08 cm) water column. "Fine-tuning" adjustments by dampers 218, 219 enable satisfactory pressures for sample conditioning entering air 53 and for supply air 220 moving in duct 222. Supply air flow 220 in supply duct 222 may be split into two or more flow components moving in laboratory space supply duct 42 and instrument test zone supply duct 44 (FIG. 6). Representative volumetric supply flow rates are 2500 ft$^3$/min (70 m$^3$/min) in duct 42 and 500 feet ft$^3$/min (14 m$^3$/min) in duct 44.

The environmental parameters or conditions of gas flows supplied by ducts 42 and 44 may be equal to each other and to entering air flow 55 conditions, and such equality is achieved by simply splitting the air flowing from positive plenum 216 into three flows by use of dampers as described above: 600 ft$^3$/min (17 m$^3$/min) for sample entry 53 in conduit 57, 500 ft$^3$/min (14 m$^3$/min) in duct 44, and 2500 ft³/min (70 m³/min) in duct 42. Whereas such flow splitting is straightforward and results in equality of environmental conditions in each of the respective flow components, and is useful in many installations, each air flow component may be further conditioned, after splitting, to achieve desired, different environmental parameters in said component. To clarify and illustrate, RH in plenum 216 could be 80%, enabling 65% set points to be achieved in laboratory space 20 and test zone 46. Electrical resistance reheater 230 under the control of sensors 101 and microcontroller 100 could elevate the temperature and thereby the RH of entering air to 65%. These approaches to realizing different environmental conditions for the multiple flows having multiple purposes may be extended for all environmental parameters by appropriate use of additional control elements 60 under control of microcontroller 100.

Figure 9:
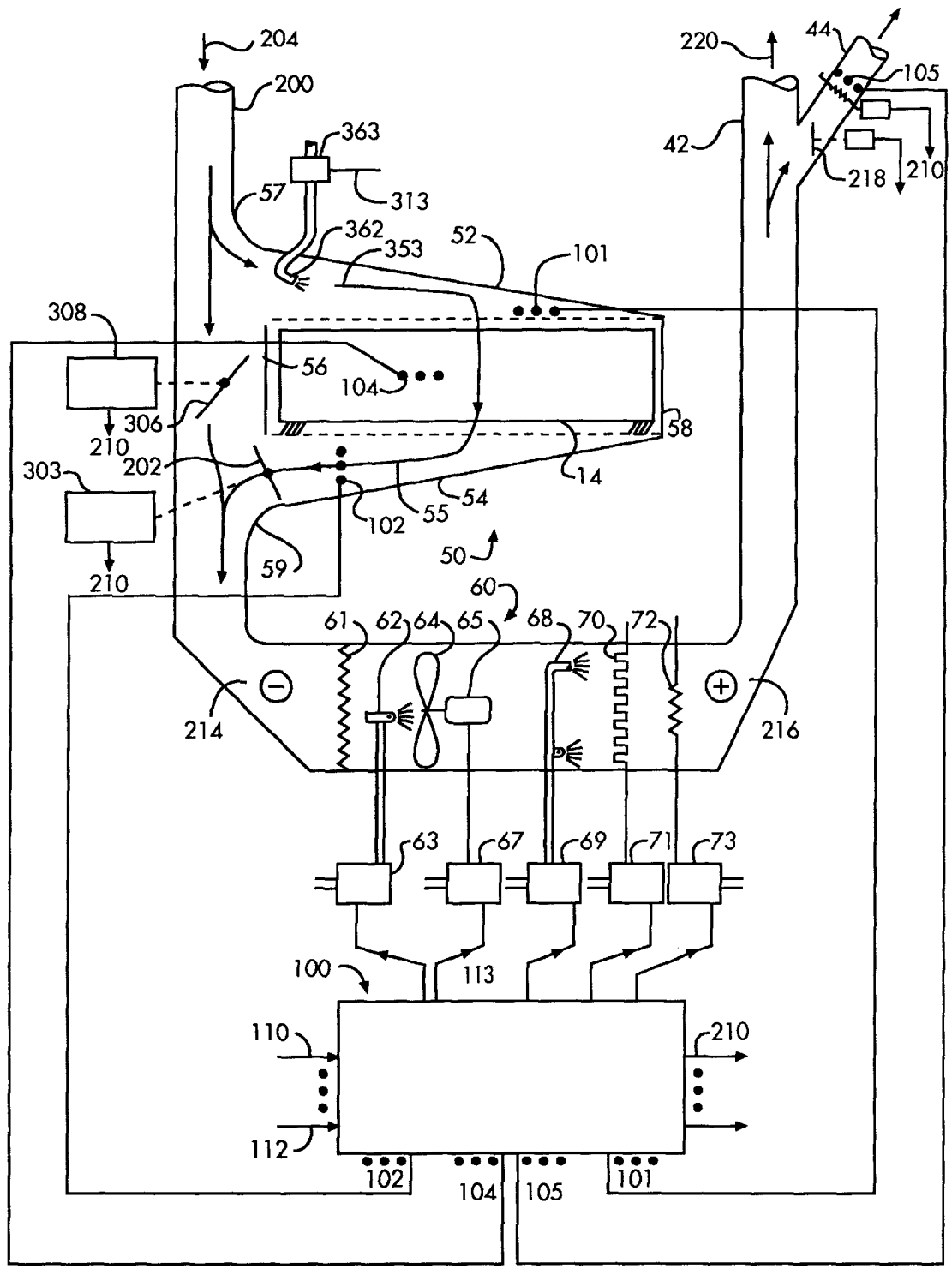
FIG. 9 depicts another embodiment as an alternative to the embodiment of FIG. 7.

Finally, FIG. 9 discloses another practical embodiment, with somewhat different air flow paths compared to the embodiment of FIG. 7. In FIG. 7, sample inlet air flow 53 is derived from the positive plenum which also provides external conditioning air flow. In FIG. 9, sample inlet air flow 353 is derived from the return air flow 204, which return air flow 204 is the same in FIGS. 6, 7 and 9.

In FIG. 9, dampers 306 and 202 realize proper suction and flows, as before. Humidifier 362 including control valve 363 actuated by signal line 313, and such other air conditioning elements as desired, condition the sample inlet air flow 353, as before. All conditioning elements, such as conditioning apparatus 60 and the various dampers, are controlled by microcontroller 100, as before.

The configuration example of FIG. 9 is typical for apparatus we intend to call "RapidAir."

In conclusion, whereas it may appear to be complicated, cumbersome, and restrictive to attempt this combination of elements for multiple conditioning purposes, we have found that the combination can achieve superior HVI test results, particularly regarding the important "oasis-zone" 20A impact, and the laboratory space 20 air conditioning costs can be half these associated with a separate laboratory space 20 air conditioner. To reiterate, our discovery began with recognition that the environmental parameters for the various purposes were reasonably compatible at the outset of our developments.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A method for conditioning a sample of cotton fiber for testing, said method comprising:

measuring sample moisture content; and based on the measured moisture content, determining a conditioning cycle and effecting the conditioning cycle by driving a conditioned gas flow through the sample;

the conditioned gas flow being conditioned as to at least one parameter selected from the group consisting of temperature, relative humidity, volume per unit of time, and time duration; and the determined conditioning cycle being a cycle which causes the sample to be conditioned to an optimum state for testing, defined as a state which produces the same test results as would be achieved by a sample passively equilibrating in an environment of 65% relative humidity and 70° F. for at least 72 hours.

2. The method of claim 1, wherein sample moisture content is measured prior to determining and effecting the conditioning cycle.

3. The method of claim 1, wherein a plurality of cotton samples are similarly measured and similarly conditioned.

4. A method for conditioning a sample of cotton fiber for testing, said method comprising:

measuring sample moisture content; and based on the measured moisture content, determining a conditioning cycle and effecting the conditioned cycle by driving a conditioned gas flow through the sample;

the conditioned gas flow being conditioned as to at least one parameter selected from the group consisting of temperature, relative humidity, volume per unit time, and time duration; and wherein the conditioning cycle includes a predetermined sequence of time intervals wherein at least one of the selected parameters varies from one time interval to the next.

5. A method for conditioning a sample of cotton fiber for testing, said method comprising:

measuring sample moisture content; and based on the measured moisture content, determining a conditioning cycle and effecting the conditioning cycle by driving a conditioned gas flow through the sample, the conditioned gas flow being conditioned as to at least one parameter selected from the group consisting of temperature, relative humidity, volume per unit time, and time duration;

wherein sample moisture content is measured concurrently with determining and effecting the conditioning cycle.

6. A method for conditioning a sample of cotton fiber for testing, said method comprising:

measuring sample moisture content; and based on the measured moisture content, determining a conditioning cycle and effecting the conditioning cycle by driving a conditioned gas flow through the sample, the conditioned gas flow being conditioned as to at least one parameter selected from the group consisting of temperature, relative humidity, volume per unit time, and time duration;

wherein twenty-four cotton samples in a perforated-bottom sample tray are similarly measured and similarly conditioned.

7. A method for conditioning a sample of fiber for testing, said method comprising;

measuring at least one property of the fiber sample selected from the group of properties consisting of weight, moisture content, nep content, trash content, fiber tenacity, fiber strength, fiber length, calorimetric properties, air flow permeability properties, near-infrared reflectance and imaged characteristics; and based on the at least one measured fiber property, determining a conditioning cycle and effecting the conditioning cycle by driving a conditioned gas flow through the sample;

the conditioned gas flow being conditioned as to at least one parameter selected from the group consisting of humidity, temperature, static pressure, pressure fluctuations, velocity, velocity fluctuations, gas composition, radioactive particle concentration, and time duration; and the determined conditioning cycle being a cycle which causes the fiber sample to be conditioned to an optimum state for testing, defined as a state which produces the same test results would be achieved by a sample passively equilibrating in a standardized environment for at least a predetermined period of time.

8. The method of claim 7, wherein the determined conditioning cycle includes the specification of temporal characteristics of at least one gas flow parameter which affects properties of the fiber sample.

9. The method of claim 7, wherein the at least one sample property is measured prior to determining and effecting the conditioning cycle.

10. A method for conditioning a sample of fiber for testing, said method comprising:

measuring at least one property of the fiber sample selected from the group of properties consisting of weight, moisture content, nep content, trash content, fiber tenacity, fiber strength, fiber length, calorimetric properties, air flow permeability properties, near-infrared reflectance and imaged characteristics; and based on the at least one measured fiber property, determining a conditioning cycle and effecting the conditioning cycle by driving a conditioned gas flow through the sample, the conditioned gas flow being conditioned as to at least one parameter selected from the group consisting of humidity, temperature, static pressure, pressure fluctuations, velocity, velocity fluctuations, gas composition, radioactive particle concentration, and time duration;

wherein the conditioning cycle includes a predetermined sequence of time intervals wherein at least one of the selected parameters varies from one time interval to the next.

11. A method for conditioning a sample of fiber for testing, said method comprising:

measuring at least one property of the fiber sample selected from the group of properties consisting of weight, moisture content, nep content, trash content, fiber tenacity, fiber strength, fiber length, calorimetric properties, air flow permeability properties, near-infrared reflectance and imaged characteristics; and based on the at least one measured fiber property, determining a conditioning cycle and effecting the conditioning cycle by driving a conditioned gas flow through the sample, the conditioned gas flow being conditioned as to at least one parameter selected from the group consisting of humidity, temperature, static pressure, pressure fluctuations, velocity, velocity fluctuations, gas composition, radioactive particle concentration, and time duration;

wherein the at least one sample property is measured concurrently with determining and effecting the conditioning cycle.

12. A method for conditioning a sample of material for testing, said method comprising:

measuring at least one material property of the sample; and based on the at least one material property, determining a conditioning cycle and effecting the conditioning cycle by driving through the sample a gas flow conditioned as to at least one parameter;

the determined conditioning cycle being a cycle which causes the sample to be conditioned to an optimum state for testing, defined as a state which produces the same test results as would be achieved by a sample passively equilibrating in a standardized environment for at least a predetermined period of time.

13. The method of claim 12, wherein the determined conditioning cycle includes the specification of temporal characteristics of at least one gas flow parameter which affects properties of the sample.

14. The method of claim 12, wherein the at least one material property is measured prior to determining and effecting the conditioning cycle.

15. A method for conditioning a sample of material for testing, said method comprising:

measuring at least one material property of the sample; and based on the at least one material property, determining a conditioning cycle and effecting the conditioning cycle by driving through the sample a gas flow conditioned as to at least one parameter;

wherein the conditioning cycle includes a predetermined sequence of time intervals wherein the at least one parameter varies from one time interval to the next.

16. A method for conditioning a sample of material for testing, said method comprising:

measuring at least one material Property of the sample; and based on the at least one material property, determining a conditioning cycle and effecting the conditioning cycle by driving through the sample a gas flow conditioned as to at least one parameter;

wherein the at least one material property is measured concurrently with determining and effecting the conditioning cycle.

17. A machine for conditioning a sample of cotton fiber for testing, said machine comprising:

a sensor for measuring sample moisture content;

a controller for determining, based on measured moisture content, a conditioning cycle which causes the sample to be conditioned to an optimum state for testing, defined as a state which produces the same test results as would be achieved by a sample passively equilibrating in an environment of 65% relative humidity and 70° F. for at least 72 hours; and gas flow conditioning apparatus for effecting the conditioning cycle by driving a conditioned gas flow through the sample, the conditioned gas flow being conditioned as to at least one Parameter selected from the group consisting of temperature, relative humidity, volume per unit time, and time duration.

18. The machine of claim 17, wherein said sensor measures sample moisture content prior to determining and effecting the conditioning cycle.

19. The machine of claim 17, wherein said sensor measures sample moisture content concurrently with determining and effecting the conditioning cycle.

20. A machine for conditioning a sample of cotton fiber for testing, said machine comprising:

a sensor for measuring sample moisture content;

a controller for determining, based on measured moisture content, a conditioning cycle which includes a predetermined sequence of time intervals wherein at least one parameter selected from the group consisting of temperature, relative humidity, volume per unit time, and time duration varies from one time interval to the next; and gas flow conditioning apparatus for effecting the conditioning cycle by driving a conditioned gas flow through the sample, the conditioned gas flow being conditioned as to the at least one parameter.

21. A machine for conditioning a sample of fiber for testing, said machine comprising:
- a sensor for measuring at least one property of the sample selected from the group of properties consisting of weight, moisture content, nep content, trash content, fiber tenacity, fiber strength, fiber length, calorimetric properties, air flow permeability properties, near-infrared reflectance and imaged characteristics;
- a controller for determining, based on the at least one property of the sample, a conditioning cycle which causes the fiber sample to be conditioned to an optimum state for testing, defined as a state which produces the same test results as would be achieved by a sample passively equilibrating in an environment of 65% relative humidity and 70° F. for at least 72 hours; and
- gas flow conditioning apparatus for effecting the conditioning cycle by driving a conditioned gas flow through the sample, the conditioned gas flow being conditioned as to at least one parameter selected from the group consisting of humidity, temperature, static pressure, pressure fluctuations, velocity, velocity fluctuations, gas composition, radioactive particle concentration, and time duration.

22. The machine of claim 21, wherein said controller determines a conditioning cycle which includes the specification of temporal and spatial characteristics of at least one gas flow parameter which affects properties of the fiber sample.

23. The machine of claim 21, wherein said sensor measures the at least one property of the sample prior to determining and effecting the conditioning cycle.

24. The machine of claim 21, wherein said sensor measures the at least one property of the sample concurrently with determining and effecting the conditioning cycle.

25. A machine for conditioning a sample of cotton fiber for testing, said machine comprising:
- a sensor for measuring at least one property of the sample selected from the group of properties consisting of weight, moisture content, nep content, trash content, fiber tenacity, fiber strength, fiber length, calorimetric properties, air flow permeability properties, near-infrared reflectance and imaged characteristics;
- a controller for determining, based on the at least one property of the sample, a conditioning cycle which includes a predetermined sequence of time intervals wherein at least one parameter selected from the group consisting of temperature, static pressure, pressure fluctuations, velocity, velocity fluctuations, gas composition, and radioactive particle concentration, and time duration varies from one time interval to the next; and
- gas flow conditioning apparatus for effecting the conditioning cycle by driving a conditioned gas flow through the sample, the conditioned gas flow being conditioned as to the at least one parameter.

26. A machine for conditioning a sample of material for testing, said machine comprising:
- a sensor for measuring at least one material property of the sample;
- a controller for determining, based on the at least one material property, a conditioning cycle which causes the sample to be conditioned to an optimum state for testing, defined as a state which produces the same test results as would be achieved by a sample passively equilibrating in a standardized environment for at least a predetermined period of time; and
- gas flow conditioning apparatus for effecting the conditioning cycle by driving through the sample a gas flow conditioned as to at least one parameter.

27. The machine of claim 26, wherein said controller determines a conditioning cycle which includes the specification of temporal characteristics of at least one gas flow parameter which affects properties of the sample.

28. The machine of claim 26, wherein said sensor measures the at least one material property prior to determining and effecting the conditioning cycle.

29. The machine of claim 26, wherein said sensor measures the at least one material property concurrently with determining and effecting the conditioning cycle.

30. A machine for conditioning a sample of material for testing, said machine comprising:
- a sensor for measuring at least one material property of the sample;
- a controller for determining, based on the at least one material property, a conditioning cycle which includes a predetermined sequence of time intervals wherein at least one parameter varies from one time interval to the next; and
- gas flow conditioning apparatus for effecting the conditioning cycle by driving through the sample a gas flow conditioned as to the at least one parameter.

31. A combination sample conditioning and air conditioning machine comprising:
- an environmental conditioning chamber within said machine for conditioning a material sample;
- at least one conditioned air discharge port for directing conditioned air to a testing laboratory space;
- at least one return air port for collecting air from the testing laboratory space; and
- gas flow conditioning apparatus for directing conditioned gas flows through said environmental conditioning chamber and out through said at least one conditioned air discharge port.

32. The combination machine of claim 31, which further comprises control elements for adjusting the gas flows through said ports.

33. The combination machine of claim 31, which further comprises:
- a sensor for measuring at least one property of the material sample; and
- a controller for determining a conditioning cycle based on the at least one property; and wherein
- said gas flow conditioning apparatus effects the conditioning cycle by driving through the sample a gas flow conditioned as to at least one parameter.

34. The combination machine of claim 31, wherein said controller determines a conditioning cycle which causes the sample to be conditioned to an optimum state for testing, defined as a state which produces the same test results as would be achieved by a sample passively equilibrating in a standardized environment for at least a predetermined period of time.

* * * * *